United States Patent [19]

Fujiwara et al.

[11] 4,401,812
[45] Aug. 30, 1983

[54] ANTHRACYCLINE ANTIBIOTICS

[75] Inventors: Akiko Fujiwara; Tatsuo Hoshino, both of Kamakura; Masaaki Tazoe, Yokohama, all of Japan

[73] Assignee: Hoffmann-La Roche Inc., Nutley, N.J.

[21] Appl. No.: 307,832

[22] Filed: Oct. 2, 1981

[30] Foreign Application Priority Data

Oct. 16, 1980 [GB] United Kingdom ................ 8033399

[51] Int. Cl.³ ...................... C07H 15/26; C12P 19/56; A61K 31/71
[52] U.S. Cl. .................................... 536/6.4; 424/181; 435/78
[58] Field of Search ............................ 536/17 A, 6.4

[56] References Cited

U.S. PATENT DOCUMENTS

| | | | |
|---|---|---|---|
| 4,039,736 | 8/1977 | Nettleton, Jr. et al. | 536/17 A |
| 4,127,714 | 11/1978 | Umezawa et al. | 536/17 A |
| 4,144,329 | 3/1979 | Umezawa et al. | 536/17 A |
| 4,207,313 | 6/1980 | Umezawa et al. | 536/17 A |
| 4,329,339 | 5/1982 | Fujiwara et al. | 536/6.4 |

FOREIGN PATENT DOCUMENTS 54-108890  2/1979  Japan ................................ 536/6.4

*Primary Examiner*—Johnnie R. Brown
*Attorney, Agent, or Firm*—Jon S. Saxe; Bernard S. Leon; Frank P. Hoffman

[57] ABSTRACT

The present invention is concerned with novel anthracyclines which are compounds of the general formula,

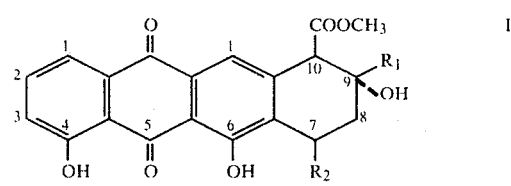

wherein $R_1$ is a methyl or acetonyl group and $R_2$ is selected from the group consisting of

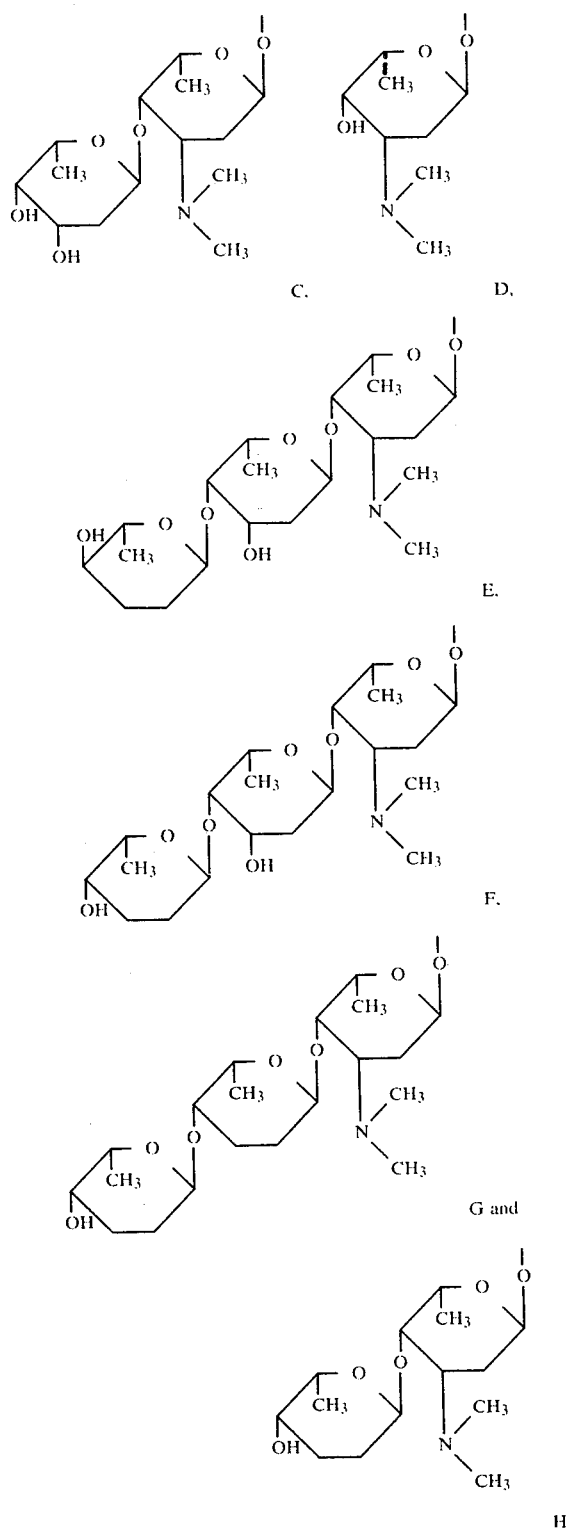

Also presented is a method of making the above compounds.

The compounds possess antibacterial and antitumor activities.

1 Claim, No Drawings

ANTHRACYCLINE ANTIBIOTICS

DESCRIPTION OF THE INVENTION

The present invention relates to novel tetracyclic compounds, to a process for the preparation thereof and to pharmaceutical preparations containing those compounds which are effective against tumors and bacteria.

More particularly, the present invention is concerned with novel anthracyclines which are compounds of the general formula,

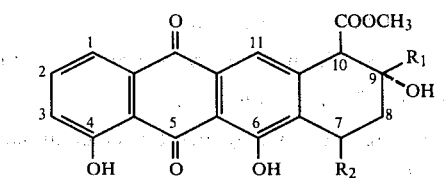

I wherein $R_1$ is a methyl or acetonyl group and $R_2$ is selected from the group consisting of

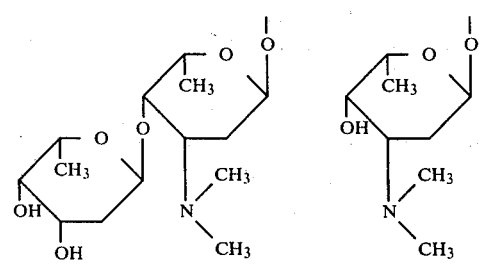

C, D,

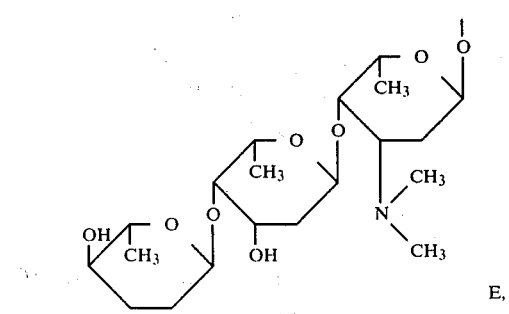

E,

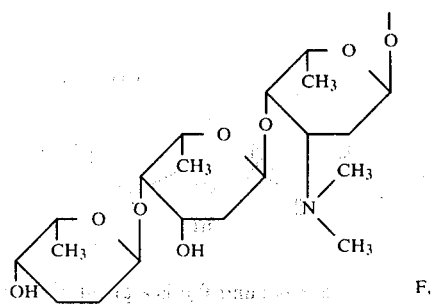

F,

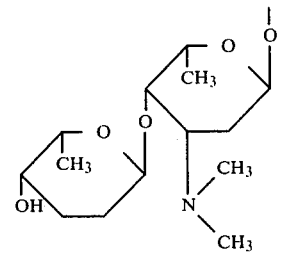

G and

H

Compounds encompassed by the above formula include:

| $R_1$ | $R_2$ | Compound |
|---|---|---|
| $CH_3$ | C | Auramycin C |
|  | D | Auramycin D |
|  | E | Auramycin E |
|  | F | Auramycin F |
|  | G | Auramycin G |
|  | H | Auramycin H |
| $-CH_2-CO-CH_3$ | C | Sulfurmycin C |
|  | D | Sulfurmycin D |
|  | E | Sulfurmycin E |
|  | F | Sulfurmycin F |
|  | G | Sulfurmycin G |
|  | H | Sulfurmycin H |

The novel compounds provided by the present invention are characterized by the following physico-chemical data. [The solvents used in thin-layer chromatography (TLC) are chloroform/methanol, 7:1, v/v (solvent A); benzene/methanol, 5:1, v/v (solvent B) and chloroform/methanol, 5:1, v/v (solvent C)]:

Auramycin C ($C_{35}H_{43}O_{13}N$)

MW: 685.3
Melting point: 151.0° C. (with decomposition)
Specific rotation: $[\alpha]_D^{20} + 78.8°$ (c=0.1 in chloroform)
TLC (Silica gel):
 Rf 0.20 (solvent A)
 Rf 0.30 (solvent B)

Auramycin D ($C_{29}H_{33}O_{10}N$)

MW: 555.2
Melting point: 139.5° C. (with decomposition)
Specific rotation: +189.3° (c=0.1 in chloroform)
TLC (Silica gel):
 Rf 0.08 (solvent A)
 Rf 0.14 (solvent B)

Auramycin E ($C_{41}H_{53}O_{15}N$)

MW: 799.9

Melting point: 157.0° C. (with decomposition)
Sepcific rotation: +32.3° (c=0.1 in chloroform)
TLC (Silica gel):
Rf 0.44 (solvent A)
Rf 0.41 (solvent B)

Auramycin F ($C_{41}H_{53}O_{15}N$)

MW: 799.9
Melting point: 160.0° C. (with decomposition)
Specific rotation: +26.7° (c=0.1 in chloroform)
TLC (Silica gel):
Rf 0.39 (solvent A)
Rf 0.38 (solvent B)

Auramycin G ($C_{41}H_{53}O_{14}N$)

MW: 783.9
Melting point: 148.5° C. (with decomposition)
Specific rotation: +38.5° (c=0.1 in chloroform)
TLC (Silica gel):
Rf 0.38 (Solvent A)
Rf 0.40 (solvent B)

Auramycin H ($C_{35}H_{43}O_{12}N$)

MW: 669.3
Melting point: 119.5° C. (with decomposition)
Specific rotation: —(not determined)
TLC (Silica gel): Rf 0.33 (solvent C)

Sulfurmycin C ($C_{37}H_{45}O_{14}N$)

MW: 727.3
Melting point: 146.0° C. (with decomposition)
Specific rotation: +55.8° (c=0.1 in chloroform)
TLC (silica gel):
Rf 0.20 (solvent A)
Rf 0.30 (solvent B)

Sulfurmycin D ($C_{31}H_{35}O_{11}N$)

MW: 597.2
Melting point: 128.0° C. (with decomposition)
Specific rotation: +167.6° (c=0.1 in chloroform)
TLC (Silica gel):
Rf 0.08 (solvent A)
Rf 0.14 (solvent B)

Sulfurmycin E ($C_{43}H_{55}O_{16}N$)

MW: 841.9
Melting point: 151.0° C. (with decomposition)
Specific rotation: +19.6° (c=0.1 in chloroform)
TLC (Silica gel):
Rf 0.38 (solvent A)
Rf 0.37 (solvent B)

Sulfurmycin F ($C_{43}H_{55}O_{16}N$)

MW: 841.9
Melting point: 151.5° C. (with decomposition)
Specific rotation: +7.9° (c=0.1 in chloroform)
TLC (Silica gel):
Rf 0.34 (solvent A)
Rf 0.36 (solvent B)

Sulfurmycin G ($C_{43}H_{55}O_{15}N$)

MW: 825.9
Melting point: 139.0° C. (with decomposition)
Specific rotation: +25.6° (c=0.1 in chloroform)
TLC (Silica gel):
Rf 0.33 (solvent A)
Rf 0.36 (solvent B)

Sulfurmycin H ($C_{37}H_{45}O_{13}N$)

MW: 711.3
Melting point: 98.5° C. (with decomposition)
Specific rotation: +59.0° (c=0.1 in chloroform)
TLC (Silica gel): Rf 0.28 (solvent C)

According to the process provided by the present invention the novel compounds of formula I hereinbefore are prepared by (a) cultivating a mutant derived from *Streptomyces galilaeus* OBB-111, capable of producing the compounds of formula I in an aqueous nutrient medium under aerobic conditions and recovering said compounds from the fermentation broth, (b) hydrolysing under acidic conditions a compound of the formula,

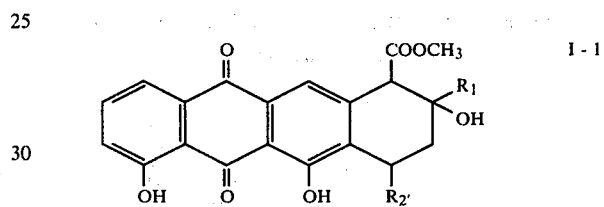

wherein $R_1$ is as above and $R_{2'}$ represents a group of formula E or F above or formula

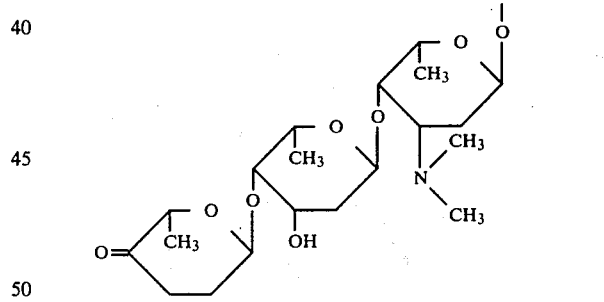

to convert the group $R_2·2'$, into the group of formula C, (c) hydrolysing under acidic conditions a compound of the formula

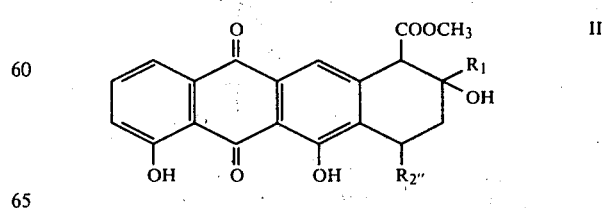

wherein $R_1$ is as above and $R_{2''}$ is a group of formula A, C, E, F or G above or formula

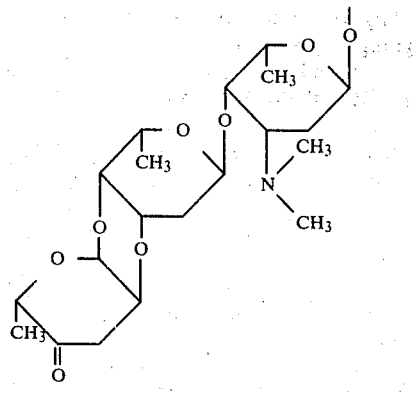

to convert the group $R_2''$ into the group of formula D, (d) hydrolysing under acidic conditions a compound of the formula,

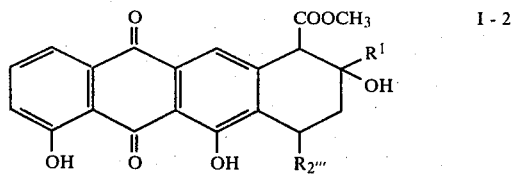

I-2 wherein $R_1$ is as above and $R_2'''$ is the group of formula G above, to convert the group $R_2'''$ into the group of formula H, (e) reducing a compound of the formula

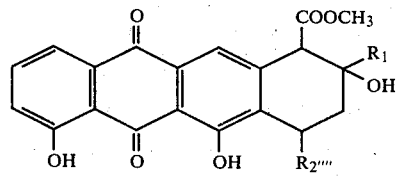

III wherein $R_1$ is as above and $R_2''''$ is the group of formula A above, to convert the group $R_2''''$ into a group of formula E or F.

The microorganism used in embodiment (a) of the foregoing process includes all mutants derived from *Streptomyces calilaeus* OBB-111, capable of producing the compounds of formula I. The strain *Streptomyces galilaeus* OBB-111 has been isolated from solids in Neuschwanstein, Oberbayern, West Germany and has been deposited in the Agency of Industrial Science and Technology, Fermentation Research Institute, Japan, under FERM-P No. 4780 (January 29, 1979), and at the American Type Culture Collection, Rockville, Md., U.S.A., under ATCC No. 31533. Such mutants derived from *Streptomyces galilaeus* OBB-111 (FERM-P No. 4780, ATCC No. 31533) can be obtained by conventional mutation methods; for example, by irradiation with UV light, X-rays or γ-rays, or by treatment with suitable mutagens.

The preferred strain used in embodiment (a) of the foregoing process is *Streptomyces galilaeus* OBB-111-610 obtained by treating *Streptomyces galilaeus* OBB-111 with N-methyl-N'-nitro-N-nitrosoguanidine. The strain *Streptomyces galilaeus* OBB-111-610 has been deposited in the Agency of Industrial Science and Technology, Fermentation Research Institute, Japan, under FERM-P No. 4883 (Mar. 22, 1979), and at the American Type Culture Collection, Rockville, Md., U.S.A., Under ATCC No. 31534.

The mycological characteristics of *Streptomyces calilaeus* OBB-111-610 (FERM-P No. 4883, ATCC No. 31534) are as follows:

1. Morphological Properties

The strain OBB-111-610 (FERM-P No. 4883, ATCC 31534) forms moderately long aerial mycelium from substrate mycelium. Hooks or spirals are observed to develop at the apex of the aerial mycelium, but no whorls are formed.

Mature spore chains with more than 10 spores per chain are usually produced. The spores are cylindrical and measures 0.5 to $0.6\mu \times 0.8$ to $1.0\mu$, and its surface is smooth.

2. Culture Characteristics on Various Media

The cultural characteristics of strain OBB-111-610 (FERM-P No. 4883, ATCC 31534) is shown in Table 1 hereinafter.

The color of the growth of strain OBB-111-610 (FERM-P No. 4883, ATCC 31534) on sucrose-nitrate agar, glucose-asparagine agar, glycerol-asparagine agar, starch-inorganic salts agar and oatmeal agar changes to pink-violet with the dropwise addition of 0.05 N sodium hydroxide solution.

TABLE 1

Cultural characteristics of strain OBB-111-610 (FERM-P No. 4883, ATCC 31534)

| Medium | Strain OBB-111-610 |
|---|---|
| Sucrose-nitrate agar | |
| Growth | pale yellow ~ pale yellowish brown [3gc, Light Tan] |
| Aerial Mycelium | brownish gray [3cb, Sand] ~ pale orange [5cb] |
| Diffusible Pigment | yellowish |
| Glucose-asparagine agar | |
| Growth | dull orange [3pe, Topaz ~ 3ne, Topaz] |
| Aerial Mycelium | light brownish gray [3dc, Natural] ~ light gray [2fe, Covert Gray] |
| Diffusible Pigment | brownish |
| Glycerol-asparagine agar (ISP medium No. 5) | |
| Growth | pale yellow [3gc, Light Tan] ~ pale yellowish brown [3lc, Amber] |
| Aerial Mycelium | light gray [2fe, Covert Gray] |
| Diffusible Pigment | yellow |
| Starch-inorganic salts agar (ISP medium No. 4) | |
| Growth | pale yellow [2pc, Bright Gold] ~ dull yellow [2pe, Mustard Gold] |
| Aerial Mycelium | light brownish gray [2dc, Natural] ~ light gray [2fe, Covert Gray] |
| Diffusible Pigment | yellow |
| Tyrosine agar (ISP medium No. 7) | |
| Growth | dark brownish gray [3ni, Clove Brown] |
| Aerial Mycelium | none |
| Diffusible Pigment | black |
| Nutrient agar | |
| Growth | colorless pale brown |
| Aerial Mycelium | none |
| Diffusible Pigment | brown |
| Yeast extract-malt extract agar (ISP medium No. 2) | |

TABLE 1-continued

Cultural characteristics of strain OBB-111-610
(FERM-P No. 4883, ATCC 31534)

| Medium | Strain OBB-111-610 |
|---|---|
| Growth | yellowish brown [3ng, Yellow Maple] |
| Aerial Mycelium | light gray [2fe, Covert Gray] |
| Diffusible Pigment | none |
| Oatmeal agar (ISP medium No. 3) | |
| Growth | pale yellowish brown [2gc, Bamboo] ~ pale brown [3ie, Camel] |
| Aerial Mycelium | light gray [2fe, Covert Gray ~ 3fe, Silver Gray] |
| Diffusible Pigment | brown |
| Skimmed milk (37° C.) | |
| Growth | brown ~ dark brown |
| Aerial Mycelium | white ~ brownish gray |
| Diffusible Pigment | dark brown |
| Glucose-peptone-gelatin agar | |
| Growth | pale yellow |
| Aerial Mycelium | none |
| Diffusible Pigment | brown |

3. Physiological Characteristics

The physiological characteristics and carbohydrate utilisation of the strain OBB-111-610 (FERM-P No. 4883, ATCC 31534) is shown in the following Tables 2 and 3, respectively. The growth temperature was examined on yeast extract-malt extract agar (ISP medium No. 2) at 20°, 27°, 32°, 37°, 40° and 45° C. Optimal temperature for growth occurs at 27° C. to 32° C. and no growth occurs at 45° C.

TABLE 2

Physiological characteristics of strain OBB-111-610
(FERM-P No. 4883, ATCC 31534)

| Test | Response | Methods and materials |
|---|---|---|
| Gelatin liquefaction | weak to moderate liquefaction | glucose-peptone-gelatin medium 27° C. |
| Starch hydrolysis | weak to moderate hydrolysis | starch-inorganic salts agar |
| Peptonisation and coagulation of skimmed milk | moderate to strong peptonisation and no coagulation | 10% skimmed milk 37° C. |
| Nitrate reduction | positive | ISP medium No. 8 27° C. |
| Melanin formation | positive | ISP medium No. 1 ISP medium No. 6 ISP medium No. 7 |

TABLE 3

Carbohydrate utilization of strain OBB-111-610
(FERM-P No. 4883, ATCC 31534)

| L-Arabinose | positive |
|---|---|
| D-Xylose | positive |
| Glucose | positive |
| D-Fructose | positive |
| Sucrose | positive |
| Inositol | positive |
| L-Rhamnose | positive |
| Raffinose | positive |
| D-Mannitol | negative |

Basal medium: Pridham-Gottlieb medium (ISP No. 9)
Temperature: 27° C.

The mycological characteristics of *Streptomyces galilaeus* OBB-111-610 (FERM-P No. 4338, ATCC 31534) are almost identical with those of the parent strain, i.e. *Streptomyces galilaeus* OBB-111 (FERM-P No. 4780, ATCC 31533).

According to a preferred aspect of embodiment (a) of the foregoing process, the compounds of formula I can be produced by cultivating *Streptomyces galilaeus* OBB-111-610 (FERM-P No. 4883, ATCC 31534) in an aqueous nutrient medium under aerobic conditions.

The cultivation may be carried out in a culture medium containing the usual nutrient substances. The carbon sources, for example, are glucose, sucrose, starch, lactose, maltose, fructose, glycerol, dextrin or mixtures thereof and the nitrogen sources are, for example, soyabean meal, cotton seed meal, meat extract, fish meal, peptone, dried yeast, cornsteep liquor, preferably wheat germ or mixtures thereof. Furthermore, if necessary, the culture medium may contain suitable inorganic substances such as phosphates, sulphates, chlorides, bromides, nitrates and carbonates of sodium, potassium, ammonium, calcium and the like.

The cultivation may be carried out in an aqueous medium under aerobic conditions, especially by a submerged fermentation process. The preferred temperature for the cultivation is in the range of 20° C. to 37° C., in particular 25° C. to 30° C. The pH of the medium may vary, but it is generally in the range of 5~8.

After the cultivation has been carried out for about 2 to 10 days under the conditions mentioned earlier, the compounds of formula I can be obtained in the fermentation broth. The compounds of formula I thus obtained i.e. auramycins C, D, E, F and G, and sulfuramycins C, D, E, F and G may be recovered from the fermentation broth; for example, by extraction with a water-immiscible organic solvent such as ethyl acetate, chloroform, methylene chloride, methyl isobutyl ketone or a mixture of chloroform and methanol, preferably with chloroform/methanol (1:1, v/v). The organic phase is separated and dried to give an oily material. A non-polar organic solvent such as n-hexane is added to this oily material, the crude compounds being thus obtained in the form of powders.

The compounds obtained can be separated from each other by chromatography on columns packed with an adsorbent such as silica gel, or with a dextran gel such as Sephadex LH-20 and the like. Fractions are analysed by thin layer chromatography and/or high pressure liquid chromatography and the appropriate fractions are combined and evaporated to give the component in more or less pure form. Further purification may be carried out by repeated column chromatography and/or by high pressure liquid chromatography.

The acid hydrolysis of auramycin A, B, C, E, F or G, or sulfurmycin A, B, C, E, F or G in accordance with embodiment (b), (c) or (d) of the foregoing process can be carried out in a manner known per se using an acid such as hydrochloric acid, sulfuric acid, phosphoric acid, hydrochloric acid-methanol and the like (0.1~3 N). The hydrolysis may be carried out at a temperature of from 0° C. to the reflux temperature of the hydrolysis mixture, preferably at an elevated temperature. Auramycin C, D and H and sulfurmycin C, D and H are prepared by this acid hydrolysis.

The reduction of the carbonyl group of the sugar moiety from auramycin A or sulfurmycin A in accordance with embodiment (e) of the foregoing process can be also carried out in a manner known per se using a reducing agent such as sodium borohydride, lithium aluminum hydride and the like, or an enzyme prepared, for example, from rat liver homogenates or cells of anthracycline antibiotic-producing microorganisms. Auramycin E and F and sulfurmycin E and F are prepared by this reduction method.

The anthracycline antibiotics prepared according to the process provided by the present invention exhibit antibacterial and antitumour activity.

Accordingly, the present invention is also concerned with antibacterial and antitumour agents which contain, as the active ingredient, an anthracycline compound of formula I. In a preferred aspect, the antibacterial agents of this invention contain auramycin or sulfurmycin C, D, E, F and/or G and the antitumor agents contain auramycin or sulfurmycin C, D, E and/or G.

The biological activities of the anthracycline compounds of this invention can be seen from the data which follow:

1. Table 4 hereinafter shows the in vitro minimum inhibitory concentrations (MIC) of auramycins C, D, E, F and G and sulfurmycins C, D, E, F and G in respect of various microorganisms determined using the agar streak method.

TABLE 4

| | MIC (μg/ml) | | | |
|---|---|---|---|---|
| Strain | Auramycin C | Auramycin D | Sulfurmycin C | Sulfurmycin D |
| *Staphylococcus aureus* 209P IAM-1011[1] | 6.25 | 12.5 | 6.25 | 25.0 |
| *Staphylococcus aureus* 209P Stf[1] | 6.25 | 12.5 | 6.25 | 25.0 |
| *Sarcina lutea* IAM1009[1] | 6.25 | 6.25 | 6.25 | 25.0 |
| *Micrococcus flavus* ATCC-10240[1] | 6.25 | 12.5 | 6.25 | 25.0 |
| *Bacillus subtilis* IAM-1027[1] | 6.25 | 12.5 | 12.5 | 12.5 |
| *Mycobacterium smegmatis* IFO-13167[1] | 6.25 | 3.13 | 3.13 | 6.25 |
| *Pseudomonas aeruginosa* IFO-12689[1] | >50 | >50 | >50 | >50 |
| *Escherichia coli* K-12 IAM-1264[1] | >50 | >50 | >50 | >50 |
| *Escherichia coli* NIHJ IFO-12734[1] | >50 | >50 | >50 | >50 |
| *Candida albicans* ATCC-10231[2] | >50 | >50 | >50 | >50 |
| *Candida tropicalis* ATCC-13803[2] | >50 | >50 | >50 | >50 |

| | MIC (μg/ml) | | | | | |
|---|---|---|---|---|---|---|
| Strain | Auramycin E | Auramycin F | Auramycin G | Sulfurmycin E | Sulfurmycin F | Sulfurmycin G |
| *Staphylococcus aureus* 209P IAM-1011[1] | 1.56 | 3.12 | 6.25 | 3.12 | 3.12 | 6.25 |
| *Staphylococcus epidermidis* IFO-12993[1] | 3.12 | 3.12 | 6.25 | 1.56 | 12.5 | 12.5 |
| *Sarcina lutea* IAM-1009[1] | 3.12 | 3.12 | 6.25 | 3.12 | 1.56 | 12.5 |
| *Micrococcus flavus* ATCC-10240[1] | 3.12 | 3.12 | 6.25 | 3.12 | 1.56 | 12.5 |
| *Bacillus subtilis* IAM-1027[1] | 3.12 | 3.12 | 12.5 | 3.12 | 3.12 | 6.25 |
| *Bacillus cereus* Ro179B[1] | 0.39 | 0.39 | 0.78 | 0.39 | 0.39 | 0.39 |
| *Escherichia coli* K-12 IAM-1264[1] | >50 | >50 | >50 | >50 | >50 | >50 |
| *Escherichia coli* NIHJ IFO-12734[1] | >50 | >50 | >50 | >50 | >50 | >50 |
| *Candida albicans* ATCC-10231[2] | >50 | >50 | >50 | >50 | >50 | >50 |
| *Candida tropicalis* ATCC-13803[2] | >50 | >50 | >50 | >50 | >50 | >50 |

[1]Heart infusion agar
[2]Sabouraud dextrose agar

2. Acute Toxicity

The acute intraperitoneal $LD_{50}$ in mice judged 72 hours after a single injection of the antibiotics is about 90 mg/kg for auramycin C, auramycin D, sulfurmycin C and sulfurmycin D, 40~80 mg/kg for auramycin G and sulfurmycin G and 20~40 mg/kg for auramycin E and sulfurmycin E.

3. Antitumor Effect

The anthracycline glycosides provided by the present invention were tested against P388 leukaemia in mice. When CDF₁ mice are inoculated with 1×10⁶ cells of P388 intraperitoneally and each of the antibiotics is administered intraperitoneally on days 1, 5 and 9, the survival time of the treated mice is prolonged as shown in Table 5 hereinafter.

TABLE 5

| Antibiotic | Dose (mg/kg/day) | Mean survival (T/C, %) |
|---|---|---|
| Auramycin C | 15.0 | 128 |
| | 7.5 | 141 |
| | 3.75 | 130 |
| | 1.88 | 135 |
| Auramycin D | 15.0 | 141 |
| | 7.5 | 149 |
| | 3.75 | 103 |
| | 1.88 | — |
| Auramycin E | 12.0 | 165 |
| | 6.0 | 158 |
| | 3.0 | 139 |
| | 1.5 | 131 |
| Auramycin G | 12.0 | 119 |
| | 6.0 | 105 |
| | 3.0 | 109 |
| | 1.5 | 102 |
| Sulfurmycin C | 15.0 | 141 |
| | 7.5 | 138 |
| | 3.75 | 141 |
| | 1.88 | 131 |
| Sulfurmycin D | 15.0 | 152 |
| | 7.5 | 128 |
| | 3.75 | 135 |
| | 1.88 | 106 |
| Sulfurmycin E | 12.0 | 165 |
| | 6.0 | 150 |
| | 3.0 | 140 |
| | 1.5 | 133 |
| Sulfurmycin G | 24.0 | 144 |
| | 12.0 | 123 |
| | 6.0 | 113 |
| | 3.0 | 112 |
| | 1.5 | 104 |

As mentioned earlier, the anthracycline compounds of formula I can be used as medicaments in the form of pharmaceutical preparations. The present antitumor agents also include the pharmaceutically acceptable salts of these compounds in particular acid addition salts of conventional inorganic and organic acids; for example, inorganic acids such as hydrochloric acid and phosphoric acid; and organic acids such as acetic acid, propionic acid and succinic acid.

The present pharmaceutical preparations contain the active ingredient in association with a compatible pharmaceutical carrier. This carrier can be an organic or inorganic inert carrier material suitable for enteral, percutaneous or parenteral administration such as, for example, water, gelatin, gum arabic, lactose, starch, magnesium stearate, talc, vegetable oils, polyalkyleneglycols, petroleum jelly and the like. The pharmaceutical preparations may also contain therapeutically valuable materials other than the anthracycline antibiotics of the present invention. The pharmaceutical preparations can be made up in a solid form (e.g. as tablets, dragées or capsules) or in a liquid form (e.g. as solutions, suspensions or emulsions). The pharmaceutical preparations may be sterilised and/or may contain adjuvants such as preservatives, stabilisers, wetting agents, emulsifiers, salts for varying the osmotic pressure or buffers.

The dosage in which the active ingredient is administered depends on the route of administration, the age, weight and condition of the patient and the particuar disease to be treated. However, a typical dosage for adults is in the range of 20 mg to 30 mg per day in the case of oral or parenteral administration, preferably by intravenous injection.

The following Examples illustrate the process provided by the present invention.

EXAMPLE 1

The scraped spores from an agar slant of *Streptomyces galilaeus* OBB-111-610 (FERM-P No. 4883, ATCC 31534) were transferred to a 500 ml Erlenmeyer flask containing 100 ml of sterilised medium consisting of 20.0 g of D-glucose, 20.0 g of soluble starch, 5.0 g of S-3 meat (Ajinomoto Co., Ltd.), 2.5 g of yeast extract (Daigo Eiyo-Kagaku Co., Ltd.), 1.0 g of dipotassium hydrogen phosphate, 1.0 g of magnesium sulphate heptahydrate, 3.0 g of sodium chloride and 3.0 g of calcium carbonate made up to one liter with tap water. This vegetative culture was incubated at 27° C. on a rotary shaker set at 180 revolutions per minute. After 72 hours, 2 ml of culture was transferred to a 500 ml Erlenmeyer flask containing 100 ml of sterile production medium consisting of 20.0 g of D-glucose, 20.0 g of soluble starch, 10.0 g of pharmamedia (Traders Oil Mill Co., U.S.A.), 1.0 g of dipotassium hydrogen sulphate, 1.0 g of magnesium sulphate heptahydrate, 3.0 g of sodium chloride and 3.0 g of calcium carbonate made up to 1 liter with tap water. The culture was incubated at 27° C. for 72~96 hours on a rotary shaker set at 180 revolutions per minute. At this time, antibiotic activity of the culture filtrate and the mycelial extract, measured by the paper disc agar diffusion method using *Sarcina lutea* IAM-1009 as a test microorganism, was 22 mm and 20 mm in diameter, respectively.

The above-mentioned *Streptomyces galilaeus* OBB-111-610 (FERM-P No. 4883, ATCC 31534) was obtained by the following method.

The spores of an agar slant culture of *Streptomyces galilaeus* OBB-111 (FERM-P No. 4780, ATCC-31533) was suspended in 10 ml of sterile physiological saline solution and filtered through a glass filter No. 3. The spore suspension was diluted 2-fold with 0.2 M tris buffer (pH 9.0) containing 2 mg/ml of N-methyl-N'-nitro-N-nitrosoguanidine and incubated at 27° C. for 60 minutes. Then the spores were collected on the Nucleopore filter (0.2 μm pore size), washed with 30 ml of sterile physiological saline solution and resuspended in 10 ml of sterile physiological saline solution. The spore suspension thus obtained was spread on the ISP-No. 2 medium in a Petri disk and incubated at 27° C. for 4~6 days. The colonies were picked up and transferred to an agar slant and incubated for 10~14 days.

EXAMPLE 2

600 ml of the vegetative culture obtained in a manner analogous to that described in Example 1 were transferred to a 50 liter jar containing 30 liters of sterile production medium containing the same components as described in Example 1 and including 0.1% Nissan Disfoam (Nippon Yushi Co., Ltd.). The cultivation was carried out at 27° C. with the agitation of 350 revolutions per minute and aeration of 1 v/v medium. After approximately 90 hours, the production of antibiotics reached the maximum.

EXAMPLE 3

(a) 240 liters of the culture were obtained in a manner analogous to that described in Example 2 using eight 50 liter jars. The culture was centrifuged. The filtrate and the cake thus obtained were extracted separately. The cake was suspended in 60 liters of methanol, stirred for 3 hours and filtered, and the cake was further extracted with methanol once again. To the extract thus obtained, 120 liters of chloroform and 120 liters of water were added and mixed, and the chloroform layer was separated. On the other hand, the culture filtrate was extracted with 480 liters of a solvent mixture of chloroform and methanol (1:1) and the chloroform layer was separated. The chloroform extracts from the cell cake and the culture filtrate were combined and evaporated to a small volume (300~400 ml). The concentrate was diluted with n-hexane to precipitate a yellow solid which was dried in vacuo to give 37.0 g of a mixture of auramycin C, auramycin D, auramycin E, auramycin F, auramycin G, sulfurmycin C, sulfurmycin D, sulfurmycin E, sulfurmycin F and sulfurmycin G.

(b) Fractionation of the foregoing mixture was carried out. Sephadex LH-20 soaked for 15 hours in a solvent mixture of chloroform and methanol (2:1) was packed into a column of 80.0 cm length and 8.0 cm diameter. The mixture obtained according to the preceding paragraph (37.0 g) was dissolved in 50 ml of a mixture of chloroform and methanol (2:1) and applied to the column. The column was eluted with a mixture of chloroform and methanol (2:1). The fractions that contained the anthracycline glycosides, analyzed by thin layer chromatography on silica gel (chloroform:methanol, 10:1), were concentrated to dryness in vacuo yielding 16.8 g of a yellow solid. This yellow solid contained auramycins C, G and sulfurmycins C, G and minor quantities of auramycins D, E, F and sulfurmycins D, E and F.

(c) The yellow solid (16.8 g) was dissolved in 20 ml of chloroform and applied to a column of 50.0 cm length and 5.0 cm diameter packed with silica gel. After washing the column with a solvent mixture of chloroform and methanol (97:3), auramycins C, G and sulfurmycins C and G were eluted with a mixture of chloroform and methanol (95:5~92:8). This eluate was concentrated to dryness in vacuo to obtain 3.8 g of yellow solid.

(d) The yellow solid obtained in step (c) was dissolved in 10 ml of dichloromethane and applied to a column of 40.0 cm in length and 3.0 cm in diameter packed with silica gel. The column was developed with a solvent mixture of dichloromethane and methanol (92:8). First sulfurmycin G was eluted followed by auramycin G, auramycin E, auramycin F, sulfurmycin E, sulfurmycin F, sulfurmycin C, auramycin C, auramycin D and sulfurmycin D in this order. The eluates were separated into five fractions; Fraction I, II, III, IV and V.

| Fraction No. | Main components included |
|---|---|
| Fraction I | sulfurmycin G |
| Fraction II | sulfurmycin G, auramycin G, auramycin E, auramycin F, sulfurmycin E, sulfurmycin F, sulfurmycin C |
| Fraction III | sulfurmycin C, auramycin C |
| Fraction IV | auramycin C |
| Fraction V | auramycin D, sulfurmycin D |

Each of the fractions was concentrated to dryness in vacuo, and 595 mg of Fraction I, 890 mg of Fraction II, 914 mg of Fraction III, 448 mg of Fraction IV and 200 mg of Fraction V were obtained in the form of yellow powders.

(e) Fraction I (595 mg) obtained in step (d) was further purified by preparative liquid chromatography. The sample was dissolved in 10 ml of a solvent mixture of dichloromethane and methanol (96:4) and chromatographed on Prep PAK-500/SILICA (Waters Associates, Inc.). The mobile phase was a 96:4 mixture of dichloromethane and methanol at a flow rate of 50 ml/min. The elution was monitored using a refractive index monitor. The fractions containing only sulfurmycin G were collected and concentrated in vacuo to a small volume. Addition of some n-hexane caused precipitation of 123 mg of pure sulfurmycin G.

(f) Fraction II (890 mg) obtained in step (d) was purified by the method described in step (e). The mobile phase was a dichloromethane:methanol mixture (96:4) at a flow rate of 50 ml/min. Sulfurmycin G eluted first and auramycin G, E, F and sulfurmycin E, F, C next. The fractions containing pure sulfurmycin G, auramycin G, E, F and sulfurmycin E, F, C were concentrated in vacuo to small volumes. Addition of n-hexane to the concentrates yielded 44 mg of pure sulfurmycin G, 25 mg of pure auramycin G, 12 mg of pure auramycin E, 13 mg of pure auramycin F, 13 mg of pure sulfurmycin E, 18 mg of pure sulfurmycin F and 95 mg of pure sulfurmycin C.

(g) Fraction III (914 mg) obtained in step (d) was purified by the method described in step (a). The mobile phase was dichloromethane:methanol (95:5) at a flow rate of 50 ml/min. Sulfurmycin C fractions were eluted first and auramycin C fractions next. The fractions containing pure sulfurmycin C and auramycin C were concentrated in vacuo to small volumes. Addition of n-hexane to the concentrates yielded 95 mg of pure sulfurmycin C and 15 mg of pure auramycin C.

(h) Fraction IV (448 mg) obtained in step (d) was further purified by thin layer chromatography (chloroform:methanol, 7:1). The band containing auramycin C was scraped off and extracted with a solvent mixture of chloroform and methanol (10:1) and concentrated in vacuo to small volumes. Addition of n-hexane to the concentrate yielded 57 mg of pure auramycin C.

(i) Fraction V (200 mg) obtained in step (d) was further purified by thin layer chromatography (chloroform:methanol 4:1). The bands containing only auramycin D or sulfurmycin D were scraped off and extracted with a solvent mixture of chloroform and methanol (8:1) and concentrated in vacuo to small volumes. Addition of n-hexane to the concentrate yielded 7 mg of auramycin D and 11 mg of sulfurmycin D.

EXAMPLE 4

A solution of 100 mg of auramycin E in 25 ml of 0.5% hydrochloric acid was hydrolysed at room temperature for 25 minutes. The reaction mixture was neutralised by dilute sodium hydroxide solution and extracted with 50 ml of chloroform twice. Combined extracts were concentrated to a small volume in vacuo and chromatographed with thin layer chromatography plates (chloroform:methanol, 5:1). The band containing auramycin C was scraped off and extracted with a solvent mixture of chloroform and methanol (4:1) and concentrated in vacuo to a small volume. Addition of some n-hexane caused precipitation of 54 mg of pure auramycin C.

EXAMPLE 5

In a manner analogous to that described in Example 4, using 100 mg of auramycin F, there were obtained 48 mg of auramycin C.

EXAMPLE 6

In a manner analogous to that described in Example 4, using 100 mg of sulfurmycin E, there were obtained 51 mg of sulfurmycin C.

EXAMPLE 7

In a manner analogous to that described in Example 4, using 100 mg of sulfurmycin F, there were obtained 45 mg of sulfurmycin C.

EXAMPLE 8

A solution of 100 mg of auramycin A in 50 ml of 0.5% hydrochloric acid was hydrolyzed at room temperature for 40 minutes. The reaction mixture was neutralised by dilute sodium hydroxide solution and extracted with 100 ml of chloroform twice. The chloroform extracts were combined and concentrated in vacuo to a small volume. The concentrate was chromatographed with thin layer chromatography plates (chloroform:methanol, 5:1). The bands containing auramycin C and D were scraped off, extracted with a solvent mixture of chloroform and methanol (4:1) and concentrated in vacuo to dryness to give 12 mg of pure auramycin C and 35 mg of auramycin D.

EXAMPLE 9

In a manner analogous to that described in Example 8, using 100 mg of sulfurmycin A, there were obtained 13 mg of sulfurmycin C and 33 mg of sulfurmycin D.

EXAMPLE 10

To a solution of 100 mg of auramycin A in 20 ml of acetone and 1 ml of methanol was added 1 ml of 0.2 N hydrochloric acid-methanol with stirring and reacted at room temperature for 40 minutes. The reaction mixture was neutralised by dilute sodium hydroxide solution and 20 ml of water was added and extracted with 20 ml of chloroform twice. The extracts were combined and concentrated to a small volume in vacuo. The concentrate was chromatographed by a column packed with silica gel (chloroform:methanol, 95:5). The fractions containing auramycin D were concentrated in vacuo to give 43 mg of auramycin D.

EXAMPLE 11

In a manner analogous to that described in Example 10 using 100 mg of auramycin E, there were obtained 41 mg of auramycin D.

EXAMPLE 12

To a solution of 100 mg of auramycin B in 15 ml of acetone was added 0.3 ml of concentrated hydrochloric acid and hydrolysed at room temperature for 120 minutes. The reaction mixture was neutralised by dilute sodium hydroxide solution and 20 ml of water was added and extracted with 20 ml of chloroform twice. The extracts were combined and concentrated to a small volume in vacuo. The concentrate was chromatographed by a column packed with silica gel (chloroform:methanol, 95:5). The fractions containing auramycin D were concentrated in vacuo to give 38 mg of auramycin D.

EXAMPLE 13

A solution of 100 mg of auramycin C in 50 ml of 0.5% hydrochloric acid was hydrolysed at room temperature for 60 minutes. The reaction mixture was neutralised by dilute sodium hydroxide solution, extracted with 100 ml of chloroform twice and concentrated in vacuo to a small volume. The concentrate was chromatographed with thin layer chromatography plates (chloroform:methanol, 5:1). The band containing auramycin D was scraped off and extracted with a solvent mixture of chloroform and methanol (4:1) and concentrated in vacuo to dryness yielding 72 mg of auramycin D.

EXAMPLE 14

A solution of 80 mg of auramycin G in 4 ml of 0.1 N hydrochloric acid was hydrolysed at room temperature for 15 minutes. The reaction mixture was neutralised by dilute sodium hydroxide solution, extracted with 4 ml of ethylacetate twice and concentrated in vacuo to a small volume. The concentrate was chromatographed with thin layer chromatography plates (chloroform:methanol, 5:1). The bands containing auramycin H and auramycin D were scraped off and extracted with a solvent mixture of chloroform and methanol (10:1). Each extract was concentrated to a small volume and addition of some n-hexane caused precipitation of 16 mg of auramycin H and 12 mg of auramycin D.

EXAMPLE 15

In a manner analogous to that described in Example 10, using 100 mg of sulfurmycin A, there were obtained 47 mg of sulfurmycin D.

EXAMPLE 16

In a manner analogous to that described in Example 11, using 100 mg of sulfurmycin F, there were obtained 44 mg of sulfurmycin D.

EXAMPLE 17

In a manner analogous to that described in Example 12, using 100 mg of sulfurmycin B, there were obtained 39 mg of sulfurmycin D.

EXAMPLE 18

In a manner analogous to that described in Example 13 using 100 mg of sulfurmycin C, there were obtained 68 mg of sulfurmycin D.

EXAMPLE 19

In a manner analogous to that described in Example 14, using 80 mg of sulfurmycin G, there were obtained 19 mg of sulfurmycin H and 13 mg of sulfurmycin D.

EXAMPLE 20

To a solution of 500 mg of auramycin A in 20 ml of ethylacetate was added 50 mg of sodium borohydride in 20 ml of water with stirring. Reduction was carried out at room temperature for 20 minutes with stirring. The reaction mixture was washed with 20 ml of water twice, dehydrated over sodium sulfate and concentrated in vacuo to a small volume. The concentrate was chromatographed with thin layer chromatography plates (chloroform:methanol:ammonium hydroxide 400:30:3). The bands containing auramycin E and auramycin F were scraped off and extracted with a solvent mixture of chloroform and methanol (5:1). Each of the extracts was concentrated to a small volume and the addition of some n-hexane caused precipitation of 200 mg of auramycin E and 50 mg of auramycin F.

EXAMPLE 21

In a manner analogous to that described in Example 20, using 500 mg of sulfurmycin A, there were obtained 162.5 mg of sulfurmycin E and 30.5 mg of sulfurmycin F.

EXAMPLE 22

A solution of 200 mg of a mixture of auramycin A and sulfurmycin A in 50 ml of 0.5% hydrochloric acid was hydrolysed at room temperature for 60 minutes. The reaction mixture was neutralised with dilute sodium hydroxide and extracted with 50 ml of chloroform twice. Combined extracts were concentrated in vacuo to a small volume and chromatographed with thin layer chromatography plates (chloroform:methanol, 5:1). The bands containing auramycin C, auramycin D, sulfurmycin C and sulfurmycin D were scraped off and extracted with a solvent mixture of chloroform and methanol (4:1), respectively. Each of the extracts was concentrated in vacuo to a small volume and the addition of some n-hexane caused precipitation of 10 mg of auramycin C, 25 mg of auramycin D, 11 mg of sulfurmycin C and 27 mg of sulfurmycin D.

EXAMPLE 23

In a manner analogous to that described in Example 22, using a mixture of 200 mg of auramycin B and sulfurmycin B, there were obtained 25 mg of auramycin D and 35 mg of sulfurmycin D.

EXAMPLE 24

Male Wistar rats were killed by decapitation. Livers were excised and homogenised with a glass Telfon homogeniser in 9.15 M potassium chloride solution and centrifuged at 9000×G for 10 minutes. The supernatant liquid was used for an enzyme preparation. A mixture consisting of 40 ml of enzyme preparation, 2 ml of a solution of auramycin A (10 mg/ml), 30 mg of NADP and 5 ml of 0.1 M Tris-HCl buffer (pH 7.8) was incubated at 37° C. for 60 minutes aerobically. The reaction was terminated by the addition of a solvent mixture of chloroform and methanol (1:1). The chloroform layer was separated, concentrated in vacuo to a small volume. The concentrate was chromatographed with thin layer chromatography plates (chloroform:methanol:ammonium hydroxide, 400:30:3), compared with authentic samples of auramycin E and auramycin F. The formation of auramycin E and auramycin F from auramycin A by rat liver enzyme was confirmed.

EXAMPLE 25

In a manner analogous to that described in Example 24, using sulfurmycin A as a substrate, the formation of sulfurmycin E and sulfurmycin F from sulfurmycin A by rat liver enzyme was confirmed.

What is claimed:

1. A compound of the formula,

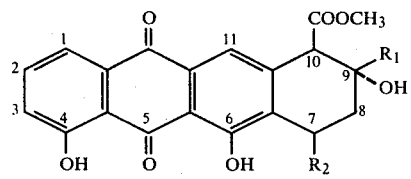

I wherein $R_1$ is an acetonyl group and $R_2$ is selected from the group consisting of

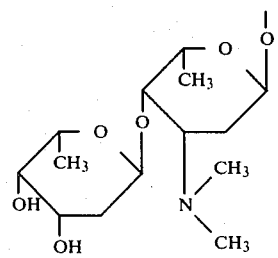 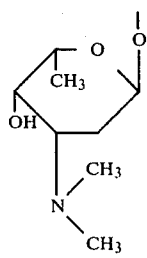

C, D,

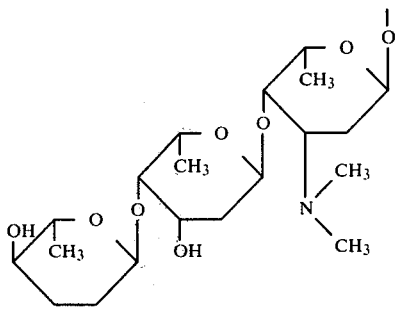

E,

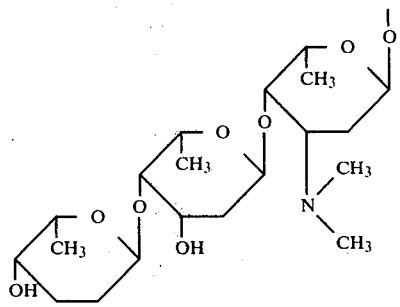

F,

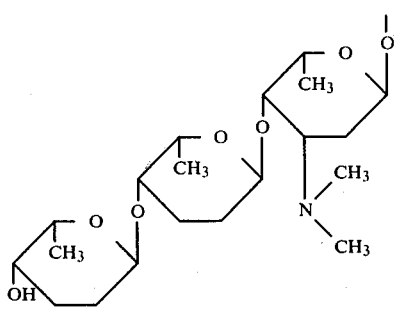

G and

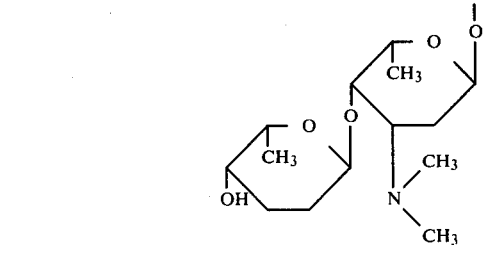

H

* * * * *